United States Patent [19]

Onwunaka et al.

[11] Patent Number: 5,281,677
[45] Date of Patent: Jan. 25, 1994

[54] THERMOPLASTIC POLYURETHANE BLENDS

[75] Inventors: Theo O. Onwunaka, Miamisburg, Ohio; Fidelis C. Onwumere, Woodbury, Minn.; James M. Lambert, Miamisburg, Ohio

[73] Assignee: Becton, Dickinson and Company, Franklin Lakes, N.J.

[21] Appl. No.: 940,274

[22] Filed: Sep. 3, 1992

[51] Int. Cl.$^5$ ............................................. C08L 83/10
[52] U.S. Cl. ................................. 525/458; 525/424; 525/440; 525/453; 525/454; 525/457; 604/264; 264/209.1
[58] Field of Search ................... 525/457, 458; 264/209.1

[56] References Cited

U.S. PATENT DOCUMENTS

| | | |
|---|---|---|
| Re. 31,873 | 4/1985 | Howes . |
| 4,454,309 | 6/1984 | Gould et al. . |
| 4,657,024 | 4/1987 | Coneys . |
| 4,781,703 | 11/1988 | Walker et al. . |
| 4,861,830 | 8/1989 | Ward, Jr. ................ 525/92 |
| 4,994,047 | 2/1991 | Walker et al. . |
| 5,004,456 | 4/1991 | Botterbusch et al. . |
| 5,061,254 | 10/1991 | Karakelle et al. . |

Primary Examiner—James J. Seidleck
Assistant Examiner—Mary Critharis
Attorney, Agent, or Firm—Richard E. Brown

[57] ABSTRACT

A thermoplastic polyurethane chain extended with an alkylenediol is blended with a thermoplastic polyurethane chain extended with an oxyalkylene qlycol oligomer. The blend is extruded into a catheter tubing having sufficient initial stiffness for satisfactory insertion in a patient and a high degree of softening for safe positioning and long term catheterization procedures without the risk of vessel wall perforation.

10 Claims, No Drawings

THERMOPLASTIC POLYURETHANE BLENDS

BACKGROUND OF THE INVENTION

1. Field of the Invention.

This invention relates to catheterization of a patient and more particularly relates to a catheter from a blend of particular polyurethanes having a desirable balance of initial stiffness and softening when contacted by a body fluid.

2. Background of the Invention.

Catheterization procedures conventionally include puncture of a patient's skin and insertion of the catheter into a body cavity, such as the blood stream, using some sort of insertion device. For patient comfort and safety, it is highly desirable that the catheter be as soft as possible to aid in advancement through a tortuous blood vessel to a desired placement while minimizing the danger of puncture of the blood vessel wall. On the other hand, the material from which the catheter is fabricated must be stiff enough for skin puncture and advancement into a blood vessel without collapsing or kinking.

A number of polymeric materials have been investigated for fabrication of catheter tubing. Silicone rubber has been used, but this material, which is soft and pliable, requires inclusion of various additives such as fillers and plasticizers to give sufficient tensile strength and other desirable properties. The thick wall needed to prevent collapse due to the pliability requires a large outside diameter to achieve sufficient inside diameter for fluid flow. the portions of the polymer molecules which include the isocyanate and extender components and generally are of high crystallinity. The soft segments form from the polyether glycol portions of the polymer chains and generally are either noncrystalline or of low crystallinity. Crystallinity and hard segment content are factors which contribute to melt processability. Gould et al., in U.S. Pat. No. 4,454,309, discloses hydrophilic polyurethane diacrylate compositions which swell in water and may be molded and cured to form shaped products. A swellable catheter fabricated of a composition which includes a nonhydrophilic component and a hydrophilic polyurethane diacrylate component is marketed by Menlo Care Inc. under the tradename STREAMLINE TM and is disclosed in U.S. Pat. Nos. 4,781,703 and 4,994,047 to Walker et al. When contacted with a liquid, the composition swells and softens due to absorption of the liquid, causing the catheter to increase in cross-sectional area.

A softening and swelling catheter fabricated of a polyurethane synthesized from polyethyleneoxide soft segment is disclosed in U.S. Pat. No. 5,061,254 to Karakelle et al. of common assignee herewith.

A multilumen catheter marketed under the tradename FLEXTIP TM by Arrow International Corp., Wilmington, Del. and disclosed by Howes in U.S. Pat. No. Re. 31,873 and by Botterbusch et al. in U.S. Pat. No. 5,004,456 consists of a relatively soft distal end segment intended for insertion into a body cavity and a relatively hard rigid portion joined thereto by heat or pressure. The catheter segments are polyurethanes from aliphatic or aromatic diisocyanates.

Other catheters of the prior art have been made of rigid substantially inflexible polymeric materials. Exemplary of such conventional catheters are the catheters of fluorinated ethylene propylene copolymer (FEP) having stripes of FEP containing a radiopaque agent disclosed by Coneys in U.S. Pat. No. 4,657,024.

In recent years, polyurethanes have come to the fore as the preferred polymeric biomaterials for fabrication of various medical device components. Polyurethanes are synthesized from three basic components, a polyisocyanate, a polyglycol and an extender, usually a low molecular weight diol, diamine or water. If the extender is a diol, the polyurethane consists entirely of urethane linkages. If the extender is water or a diamine, both urethane and urea linkages are present. ·

The usual polyglycols are polyethylene qlycol (PEG) and polytetramethylene ether glycol (PTMEG). Polypropylene ether glycol (PPG), while providing a polyurethane of a desirable high softness, is infrequently used for polyurethanes intended for medical use because PPG requires a catalyst for reaction with isocyanates. The usual catalysts for polyurethane synthesis, such as octyl stanoate and dibutyl tin dilaurate, are toxic and contraindicated for medical grade polyurethane synthesis because of the danger of leachinq into a patient's body fluid.

Polyurethanes develop microdomains conventionally termed hard segments (HS) and soft segments, and as a result are often referred to as segmented polyurethanes. The hard segments form by localization of A different approach to softening is disclosed in U.S. patent application Ser. No. 07/499,145 of common assignee herewith. A catheter of controlled softening is achieved by encapsulating a stripe of a hydrophobic stiffening polymer in a tubing of a hydrophilic thermoplastic base polymer.

While significant improvement in catheter performance has resulted from the above disclosures, there remains a need for a one piece catheter having the blood compatibility, softness and pliability of polyurethane which retains sufficient mechanical strength and stiffness for ease of insertion and repositioning if desired. The present invention addresses this need.

SUMMARY OF THE INVENTION

A nonswellinq blend of polyurethanes includes a thermoplastic polyurethane (TPU) chain extended with an oxyalkylene glycol oligomer and a TPU chain extended with an alkylene glycol. Preferred polyurethanes are chain extended with triethylene glycol (TEG) and 1,4 butanediol (BDO). Both TPUs additionally contain a polyisocyanate and a polymeric soft segment. The preferred polyisocyanate is diphenylmethane-4,4'-diisocyanate (MDI) and the preferred soft segment is a substantially nonhydrophilic polyether, most preferably PTMEG, or an amine terminated polypropylene oxide glycol. The blend may contain other materials such as a radiopaque agent or an anti-infective agent, and may be extruded into a tubing. The preferred tubing is a catheter tubing which may contain any number of lumens. The most preferred catheter is trilumen and contains a radiopaque agent. The extruded tubing may be coated with an anti-thrombogenic agent or an antibiotic.

The catheter fabricated from the blend of the invention is initially stiff but softens up to 87% in 37° C. normal saline compared to softening of about 60% for catheters of the prior art. The high initial stiffness is highly advantageous for catheter insertion in a patient. The high softness after contact with a body fluid provides flexibility which aids positioning and reduces the risk of vessel wall perforation. The nonswelling feature of the disclosed catheter is particularly important for central venous applications. In such applications, the catheter is placed close to the heart and is subject to continual motion due to the beating of the heart. As a result, a problem in central venous catheterization has been irritation of the vessel wall due to continual rubbing by the catheter wall. This condition can lead to phlebitis and hemorrhage. Swellable catheters which increase in lumen size bring catheter and vessel walls closer together and exacerbate this problem. In peripheral catheterization these events are not a serious problem because the many smaller blood vessels in the catheterized area are quickly able to bypass the affected area.

The blend of the invention offers advantages over commercially used catheter materials such as TECOFLEX TM or PELLETHANE TM because excellent tensile strength with concommitant softening is achieved by a process which is free of potentially leachable toxic catalysts or processing aids. In contrast to prior art catheters, the initial stiffness combined with the high softening after insertion allows a catheter to be manufactured as a one-piece unit with no joints which may come apart during use and leave a catheter section free inside a patient.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments described. The scope of the invention will be measured by the appended claims and their equivalents.

The novel blend of polyurethanes of the invention may be used in a number of applications requiring soft, elastomeric, blood compatible, and tissue compatible polymers. For example, they have applicability in long term implantable catheters which require stiffness for insertion but softness for patient comfort and safety during advancement through a tortuous blood vessel. They may also be useful for products such as vascular grafts, hemodialysis catheters, introducer, urinary and peripheral catheters, and obturators. They are particularly suitable for virtually all central venous access catheter products in which swelling after insertion would be detrimental.

In accordance with the present invention, a melt processable polyurethane mixture having a desirable balance between stiffness and softness is obtained by blending polyurethanes synthesized from particular diol chain extenders. The polyurethanes blended in the invention also include conventional polyisocyanates and soft segments.

Polyisocyanates useful in the present invention may have two or more isocyanate groups. Preferred polyisocyanates are aromatic or alicyclic diisocyanates, such as MDI, toluene diisocyanate, isophorone diisocyanate, 4,4'-dicyclohexyl-methane diisocyanate, hexamethylene diisocyanate and the like. Of these, aromatic diisocyanates are preferred, most preferably MDI.

The soft segments of the polyurethanes may preferably be substantially nonhydrophilic polyether glycols having a molecular weight of 500-16,000. The most preferred polyglycol is PTMEG having a molecular weight of about 400 to 4,000, preferably about 500 to 3,000, most preferably about 650 to 1,000. These products are available commercially under the trade names POLYMEG TM (Quaker Oats Co., Chemical Division) and TERATHANE TM (Dupont), respectively. Because the soft segment is nonhydrophilic, the polyurethanes in the blend do not swell in contact with the blood. Nonswelling is a particularly important feature of the blend which makes catheters fabricated from the blend particularly suitable for central venous applications.

The soft segments may optionally also contain an amine terminated polyether. These products are commercially available under the trade name JEFFAMINE TM from Texaco Chemical Co. (Bellair, Texas). These products are hereinafter designated as JA and may include repeating units of polyalkylene oxide having a molecular weight of about 400 to 8,000. Preferred JAs have polypropylene oxide repeating units. The most preferred JA is an amino terminated polypropylene oxide having a molecular weight of about 4,000 sold under the trade name JEFFAMINE TM D 4000. When the soft segment contains JA, the ratio of the polyglycol and the JA may be about 10:1 to 1:10, preferably about 4:1 to 1:1, most preferably about 2:1 to 1:1. (All percentages and ratios in this disclosure are by weight unless otherwise specified.)

The first TPU of the blend, hereinafter referred to as TPU-BDO, is a stiffening component and may be chain extended with an alkylenediol such as ethanediol, 1,6-hexanediol, 1,8-octanediol, and 1,10-decanediol, most preferably with BDO. The second TPU of the blend is a softening component and may be chain extended with an oxyalkylene qlycol oligomer. Preferred oligomers have 5 to 9 carbon atoms. The most preferred oligomer is TEG, and is hereinafter referred to as TPU-TEG. Other suitable oligomers are, for example, dipropylene glycol, tripropylene glycol and tetraethylene qlycol. Both polyurethanes may have a hard segment content of about 40-70 percent, preferably about 55-65%. The blend may contain from about 30-70% of TPU-BDO and about 70-30% of TPU-TEG, based on total polyurethane. The preferred blend contains about 35 to 45% of TPU-BDO and about 65 to 55% of TPU-TEG.

In synthesizing the polyurethanes of the invention, the ratio of the ingredients which may be used is based on the reaction of one isocyanate group with one alcohol or amino group from the polyglycol, JA or extender. Thus, the ratio of the total isocyanate groups in the diisocyanate to the total hydroxyl and amino groups present is conventionally referred to as the isocyanate index (II) and may be from about 1.00 to 1.30 preferably from about 1.00 to 1.05, most preferably about 1.02. The quantities of the ingredients to be mixed may be calculated from the predetermined ratio of desired hard and soft segments and the known equivalent weights of the diisocyanate, polyglycol, JA and extender. Synthesis of the polymer of the invention may be carried out by either a catalyst-free two step or prepolymer method or preferably by a catalyst-free one shot or bulk method. In the prepolymer method, the soft segment components are reacted with the diisocyanate to give a prepolymer having terminal isocyanate groups. The isocyanateterminated prepolymer may then be reacted with the chain extender.

In one preferred bulk polymerization process of the invention, conventional polymerization equipment is charged with the extender and soft segment in proportions predetermined in accordance with the desired hard segment soft segment ratio. With vigorous stirring, the diisocyanate may be added all at once. If the reaction does not start spontaneously, the mixture may be heated sufficiently to induce an exothermic reaction. The reaction mixture may be stirred vigorously until the exotherm is complete and the temperature begins to drop off, generally for about 1 to 5 minutes. The clear homogeneous melt, while still hot, may advantageously be removed from the reactor prior to curing. This procedure is described in detail in Example I.

In an alternative procedure, the soft segment and diisocyanate may be mixed with stirring, and, when the initial exotherm begins to subside, the extender may be added with continued stirring.

The reaction may be carried out for about 1 second to 10 minutes, preferably about 15 seconds to 5 minutes, most preferably for about 1 to 2 minutes. In general, the exotherm reaches about 100° C. before subsiding.

Any conventional method may be used to effect curing. Preferably, the melt is simply set aside for a suitable time and temperature, as, for example, from ambient to about 125° C. and for about 1 hour to 20 days.

Any polymerization equipment or technique which provides vigorous stirring of the reactants and a clear melt at the conclusion of the exotherm may be used. Preferred equipment includes a multipaddle shaft driven at high rotation rate by a motor. Exemplary of such a system is the Fluidyne Model 63014 Microshot Elastomer Processing System.

The polyurethane blend of the invention may be fabricated into an article of any desired shape such as film, tubing and other forms by conventional thermoplastic fabricating techniques including melt casting, extrusion molding, etc. The blend may have incorporated therein, as desired, conventional additives such as stabilizers, radiopaque materials such as barium sulfate, and the like. The additive may be incorporated in either or both of the polyurethanes of the blend. The radiopaque agent may be included as coextruded stripes, as is well known in the catheter art, or may be bulk distributed. The amounts of these materials will vary depending upon the application of the polyurethane, but they are typically present in amounts ranging from about 20 to 40% of the polymer blend.

The shaped article may also include an antithrombogenic agent and/or an antimicrobial agent bulk distributed into either polyurethane prior to melt processing or coated onto the article after fabrication. Representative nonlimitinq agents such as heparin, chlorhexidene and penicillin may be used. A suitable coating procedure is, for example, application of a coating of a quaternary ammonium salt to the article surface and reaction of the salt with the agent. Bulk distribution and coating procedures for antithrombogenic and antimicrobial agents are well-known in the art and no further details with respect to this aspect of the invention are needed for a full understanding of this aspect of the invention by one skilled in the art.

The preferred article of the invention is a catheter, most preferably a multilumen catheter. While the number of lumens or the size of the catheter is limited only by the extrusion die used, the most preferred catheter of the invention is a 7-French trilumen catheter.

When tested for stiffness and softening by the conventional procedure of Example III, the catheter of the invention had an initial (i.e., when dry) bend force of about 100 to 190, preferably about 110 to 160, most preferably about 120 g. After contact with normal saline for various time periods, the catheters had softened up to 90% at equilibrium (after about 30 min.) to a bend force of 10–40, preferably about 20–35, most preferably about 30 g. Further, the softening had reached about 90% of its equilibrium level after only 10 min, about the length of time required for insertion and positioning by a skilled practitioner.

Catheters having the same (60%) hard segment made by extrusion of a TPU from MDI and PTMEG but extended with BDO alone, with TPG alone, with a mixture of BDO and TEG as coextenders, and the commercial multilumen FLEXTIP TM catheter disclosed in the aforementioned U.S. Pat. No. RE 31,873, were also tested in accordance with Example III. The results of these experiments are given in Table I.

TABLE I

| | Bend Force 0 min. | Force 10 min. | (gr.) 30 min. | Softening % |
|---|---|---|---|---|
| TPU-BDO/TPU-TEG (%/%) | | | | |
| 1. 50/50 | 188 | | 32 | 83 |
| 2. 45/55 | 197 | | 32 | 84 |
| 3. 40/60 | 162 | 46 | 32 | 80 |
| 4. 35/65 | 144 | | 20 | 86 |
| 5. 30/70 | 155 | 33 | 20 | 87 |
| TPU-JA-BDO/TPU-TEG (%/%) | | | | |
| 6. 40/60 | 147 | 37 | 22 | 85 |
| 7. 45/55 | 123 | 30 | 20 | 83 |
| 8. 50/50 | 117 | | 22 | 81 |
| 9. 55/45 | 127 | | 29 | 77 |
| 10. TPU(BDO) | 230 | 112 | 92 | 60 |
| 11. TPU(TEG) | too soft as a homopolymer to insert and measure | | | |
| 12. TPU-BDO/TEG | 62 | | 23 | 63 |
| 13. FLEXTIP TM | 122 | 45 | 41 | 66 |

It is seen from Table I that the catheters of the invention containing blends of TPU-BDO and TPU-TEG have high initial bend forces. Sufficient stiffness is present in these catheters for insertion, and softening up to 87% is present for positioning. A catheter prepared from TPU-TEG alone (entry 11) is too soft initially for satisfactory insertion or further softening. A catheter prepared from TPU-BDO alone (entry 10) has high stiffness initially for insertion but its percentage of softening is significantly lower than the catheters of the invention, and is about the same as the commercial trilumen catheter sold under the tradename FLEXTIP TM. A 60% hard segment catheter made using a 50:50 mixture of BDO and TEG as coextenders (entry 12) is seen to have a low initial bend force. This catheter does not have the stiffness necessary for insertion.

The following examples are provided to further describe the invention but are not to be considered in any way to be limitative of the invention.

EXAMPLE I

Representative Polymer Syntheses

A. Synthesis of TPU-BDO of 60% hard segment

In a metal can, 480 g of PTMEG of molecular weight 1000 and 155.9 g of BDO were mixed thoroughly by stirring with a mechanical stirrer. To this mixture, 556 g of MDI was added. Vigorous stirring was continued for about 45 seconds as the exotherm approached 100° C. The hot viscous product was then poured into a TEFLON TM coated tray cured with atmospheric moisture and post cured in an oven at 125° C. for one hour.

B. Synthesis of TPU-TEG of 60% hard segment

The procedure was as in A except that TEG was used as a chain extender. The quantities of PTMEG, TEG, and MDI were 600, 276.9, and 623.2 g respectively. An exotherm of about 80° C. was reached in 78 seconds from time of addition of MDI. The product was cured as in A.

C. Synthesis of TPU-JA-BDO of 50% hard segment

The procedure was the same as was described for preparations 1 and 2 except that JEFFAMINE TM D-4000 was used as a co soft segment. The quantities of PTMEG, D-4000, BDO and MDI were 400, 200, 126.6 and 473.4 g. respectively. The PTMEG, D-4000 and BDO were mixed thoroughly before adding the MDI. Vigorous stirring was continued for about 75 seconds as the exotherm approached 100 C. The product was poured into a TEFLON TM tray and cured as above.

D. Synthesis of TPU-TEG BDO copolymer of 60% hard segment

The procedure was as in A except that a 50:50 mixture of TEG and BDO were used as the soft segment. The quantities of PTMEG,TEG,BDO and MDI were 200, 38.04, 38.04 and 223.9 g respectively. An exotherm of 115° C. was reached in 3 min. The product was cured as in A.

EXAMPLE II

Polymer Compounding and Extrusion

The cured slabs were sliced with a band saw and chipped using conventional grinding and chipping machines. Different weight ratios of polymers A and B were mixed, as was done for polymers B and C, before drying for 48 hours. Each polymer mixture was compounded with 35% barium sulfate and 0.1% yellow colorant using a twin screw extruder.

The pellets were re-dried for 48 hours and extruded into 7 French trilumen tubings with a Killon 1" Extruder, Model KL100, with L/D 24:1 and 3:1 compact ratio screw. The extruded tubings were used to determine the softening profile of the blends. The extrusion conditions used are given in Table II below.

TABLE II

| Conditions Zone Temp. F. | TPU-BDO/ TPU-TEG | TPU-JA-BDO/ TPU-TEG |
|---|---|---|
| 1 | 296 | 295 |
| 2 | 376 | 375 |
| 3 | 386 | 386 |
| 4 | 390 | 390 |
| 5 | 390 | 390 |
| 6 | 390 | 390 |
| Pump melt | 382 | 382 |
| Screw Rpm | 17 | 15 |
| Screw/Pump Amps | 6.0/— | 3.8/1.4 |
| Pump Inlet Press. | 600 | 600 |
| Pump Outlet Press. | 1000 | 700 |

EXAMPLE III

Determination of Bend Force and Percent Softening

The extruded 7 French trilumen catheter tubings were conditioned for 48 hours at 23° C. and relative humidity of 50% and immersed in a water bath at 37° C. in normal saline for various time periods. Bend forces were determined before and after immersion with an Instron Universal Testing Machine, Model 1122, equipped with an environmental chamber maintained at 37° C.

What is claimed is:

1. A melt processable nonswelling blend comprising a first polyurethane chain extended with an oxyalkylene glycol oligomer and a second polyurethane comprising an alkylene glycol chain extender and a substantially non-hydrophilic soft segment selected from the group consisting of polyetherglycol and an amine terminated polyether.

2. The blend of claim 1 wherein said oligomer is selected from the group consisting of triethylene qlycol, dipropylene glycol, tripropylene qlycol, and tetraethylene glycol.

3. A melt processable nonswelling blend comprising a first polyurethane which is the reaction product of an aromatic diisocyanate, a substantially non-hydrophilic polyetherglycol soft segment and triethylene glycol chain extender and a second polyurethane which is the reaction product of an aromatic diisocyanate, an alkylene diol chain extender and a substantially non-hydrophilic soft segment selected from the group consisting of a polyether glycol and an amine terminated polyether.

4. The blend of claim 3 in which the percentage of said first polyurethane is about 30 to 70 and the percentage of said second polyurethane is about 70 to 30.

5. The blend of claim 3 in which the hard segment content of said first and second polyurethanes is about 40 to 70.

6. The blend of claim 3 further comprising an agent selected from the group comprising a radiopaque agent, an antimicrobial agent and an antithrombogenic agent.

7. A melt processable nonswelling blend comprising a first polyurethane comprising the reaction product of an aromatic diisocyanate, polytetramethylene ether glycol and triethylene glycol and a second polyurethane which is the reaction product of an aromatic diisocyanate, polytetramethylene ether glycol and 1,4-butanediol.

8. A medical article fabricated from the blend of claim 1.

9. The article of claim 8 which is a catheter.

10. A method for preparing a softening, nonswelling tubing comprising:

a) preparing a first polyurethane comprising the reaction product of a diisocyanate, a substantially non-hydrophilic polyetherglycol and an alkylene glycol chain extender;

b) preparing a second polyurethane comprising the reaction product of a diisocyanate, a substantially non-hydrophilic polyetherglycol and an oxyalkylene glycol oligomer chain extender;

c) preparing a blend having about 30-70% by weight of said first polyurethane and about 70-30% by weight of said second polyurethane; and d) extruding said blend into a tubing.

* * * * *